US00PP12259P2

(12) United States Plant Patent
Pieters

(10) Patent No.: US PP12,259 P2
(45) Date of Patent: Dec. 11, 2001

(54) CHRYSANTHEMUM PLANT NAMED 'GEDI WO'

(76) Inventor: Dirk Pieters, Schierveldestraat 3A, Oosnieuwkerke, 8840 Staden (BE)

( * ) Notice: Subject to any disclaimer, the term of this patent is extended or adjusted under 35 U.S.C. 154(b) by 0 days.

(21) Appl. No.: 09/245,234

(22) Filed: Feb. 5, 1999

(51) Int. Cl.[7] ..... A01H 5/00
(52) U.S. Cl. ..... Plt./294; Plt./288

(58) Field of Search ..... Plt./288, 294

(56) References Cited

U.S. PATENT DOCUMENTS

P.P. 10,419 * 5/1998 Pieters ..... Plt./287

* cited by examiner

*Primary Examiner*—Howard J. Locker

(57) ABSTRACT

A new chrysanthemum plant variety producing white daisy-type flowers.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'GEDI WO'.

The new variety is a natural occurring whole plant mutation of the variety 'Ozenda' (U.S. Plant Pat. No. 10,419), discovered as part of a breeding program October 1996 in Staden, Belgium. The new variety has been asexually reproduced by vegetative cuttings in Ventura County, Calif. and the distinguishing characteristics are retained through successive generations of asexual reproduction.

SUMMARY OF THE INVENTION

'GEDI WO' is a chrysanthemum plant that produces white daisy-type flowers with slight yellow tone in center.

COMPARISON WITH PARENTS

'GEDI WO' differs from its parent in having a white flower with a slight yellow tone in the center, whereas 'Ozenda' has light lavender ray florets.

BRIEF DESCRIPTION OF ILLUSTRATION

The accompanying photograph shows a typical specimen of the plant and flowers of the new variety with colors being as nearly true as possible with an illustration of this type.

DESCRIPTION OF THE PLANT

The following description of the new variety is of specimens grown in a greenhouse in Ventura County, Calif. in the month of April. 'GEDI WO' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that longevity of individual blooms of 'GEDI WO' is about 28 days and the plant has a response time of about 7 weeks. No growth retardant has been applied in the specimens described. Useful growing conditions include night temperatures of about 18°–20° and day temperatures of about 20°–30°. The new variety is naturally blooming during late September to early October in Ventura County, Calif.

Plant:
- *Habit*.—Mounding herbaceous, free branching.
- *Height*.—About 28 cm.
- *Number of breaks from pinch*.—About 4 to 5.
- *Length of lateral branches*.—About 20 cm.
- *Stem color*.—Near 138B.

Foliage:
- *Leaf arrangement*.—Alternate.
- *Number of leaves per lateral branch*.—About 13 fully expanded leaves.
- *Leaf size*.—Length: About 5.5 cm. Width: About 3.2 cm.
- *Leaf shape*.—Ovate.
- *Attachment*.—Petioled.
- *Leaf apex*.—Acute.
- *Base*.—Tapered.
- *Margin*.—Palmately lobed.
- *Aspect*.—Slightly undulate.
- *Surface*.—Top: Pubescent. Bottom: Pubescent.

Venation: Prominent midvein on underside.
- *Color upper side*.—Near 138A.
- *Color underside*.—Near 146D.

Petiole:
- *Length*.—About 1.1 cm.
- *Color*.—Near 146D.

Color:
- *Mature leaf*.—Top: Near 137A. Bottom: Near 137D.
- *Young leaf*.—Top: Near 137A. Bottom: Near 138A.

Bloom:
- *Inflorescence form*.—Cyme.
- *Bloom type*.—Daisy-type.
- *Number of blooms per branch*.—About 15.
- *Diameter of fully expanded bloom*.—About 4 cm.
- *Depth of fully expanded bloom*.—About 1.8 cm.
- *Sepal*.—Number: About 20. Color: Near 137B. Length: About 0.6 cm. Width: About 0.3 cm.
- *Peduncle*.—Average Length: About 6 cm. Terminal: About 4 cm. Lateral: About 8 cm. Aspect: Weak, slightly undulating. Surface: Pubescent. Color: Near 137D.

Flower bud (when just showing color):
*Color*.—Near 155B.
*Diameter*.—About 0.8 cm.
*Height*.—About 0.6 cm.
*Shape*.—Slightly flattened sphere.

Ray florets:
*Number per flower*.—About 120.
*Texture*.—Matte.
*Shape*.—Oblanceolate.
*Apex*.—About 2–3 irregular obtuse lobes.
*Base*.—Tapered.
*Margin*.—Entire.
*Aspect*.—Recurved.
*Length*.—About 1.7 cm.
*Width*.—About 0.7 cm.

Disc florets:
*Number per flower*.—About 40.
*Texture*.—Shiny.
*Shape*.—Cylindric, fluted apex, disc diameter about 0.4 cm.
*Length*.—About 0.6 cm.
*Width*.—About 0.1 cm.

Fragrance: Faint.

General flower description: White daisy-type with yellow center.

Ray florets, top side:
*Immature*.—Near 158C.
*Mature*.—Near 155D.
*Fading*.—Near 155D.

Ray florets, under side:
*Immature*.—Near 158C.
*Mature*.—Near 155D.
*Fading*.—Near 155D.

Disc florets:
*Immature*.—Near 13C.
*Mature*.—Near 15B.
*Fading*.—Near 22B.

Changes as the flower ages: Ray florets become more loosely held and center disc florets become more apparent.

Reproductive organs:

Ray florets: Pistillate.
*Stigma shape*.—2 forked.
*Stigma color*.—Near 12A.
*Style length*.—About 0.4 cm.
*Style color*. —Near 154D.

Disc florets:
*Stigma shape*.—Linear.
*Stigma color*.—Near 7B.
*Style length*.—About 0.3 cm.
*Style color*.—Near 154D.
*Stamen number*.—About 5.
*Anther length*.—About 0.2 cm.
*Pollen color*.—Near 14B.
*Pollen quantity*.—Moderate.

What is claimed is:

1. A new and distinct chrysanthemum plant of the variety substantially as herein shown and described.

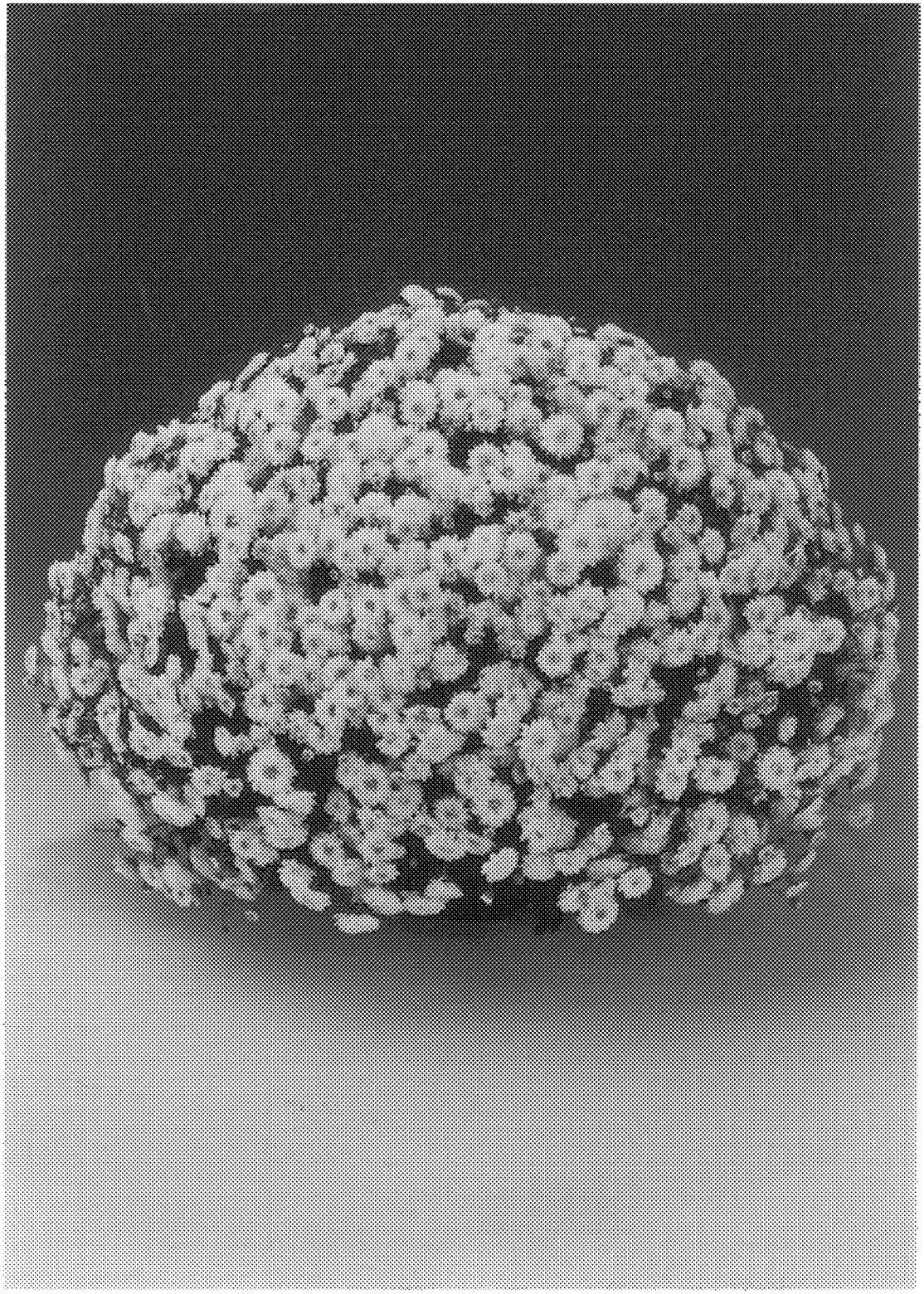

* * * * *